US00PP25441P3

(12) United States Plant Patent
Roberts

(10) Patent No.: US PP25,441 P3
(45) Date of Patent: Apr. 14, 2015

(54) MINT PLANT 'BOULDER MINT'

(50) Latin Name: ***Mentha* sp.**
Varietal Denomination: Boulder Mint

(71) Applicant: Essex Laboratories, Inc., Napavine, WA (US)

(72) Inventor: Donald D. Roberts, Independence, OR (US)

(73) Assignee: Essex Laboratories, Napavine, WA (US)

( * ) Notice: Subject to any disclaimer, the term of this patent is extended or adjusted under 35 U.S.C. 154(b) by 139 days.

(21) Appl. No.: 13/815,160

(22) Filed: Feb. 4, 2013

(65) Prior Publication Data

US 2014/0223624 P1 Aug. 7, 2014

(51) Int. Cl.
*A01H 5/00* (2006.01)

(52) U.S. Cl.
USPC ..... Plt./259

(58) Field of Classification Search
USPC ..... Plt./259
See application file for complete search history.

(56) References Cited

U.S. PATENT DOCUMENTS

PP11,788 P2 2/2001 Roberts
PP13,720 P2 4/2003 Roberts

OTHER PUBLICATIONS

PLUTO Plant Patent Database Oct. 30, 2014. p. 1.*
Gobert, V., "Hybridization in the section *Mentha* (Lamiaceae) inferred from AFLP markers," Am. J. Bot, Dec. 2002, 89 (12), pp. 2017-2023.
Fuchs, Sabine, et al., "Biosynthesis of Menthofuran in *Mentha* × *piperita*; Stereoselective and Mechanistic Studies"; J. Agric. Food Chem., 1999, 47 (10), pp. 4100-4105.
Dung, Jeremiah K.S., et al. Evaluation of Verticillium Wilt Resistance in *Mentha arvensis* and *M. longifolia* Genotypes, Plant Disease, Oct. 2010, vol. 94, pp. 1255-1260.
Verma, R.S., et al., Essential Oil Composition of Menthol Mint (*Mentha arvensis*) and Peppermint (*Mentha piperita*) Cultivars at Different Stages of Plant Growth from Kumaon Region of Western Himalaya; J. Medicinal and Aromatic Plants, India, 2010, vol. 1(1):pp. 13-18.

* cited by examiner

*Primary Examiner* — Annette Para
(74) *Attorney, Agent, or Firm* — Marger Johnson & McCollom, PC

(57) ABSTRACT

Mint selection 07-A3-5A, denominated 'Boulder Mint', is a new *Mentha* sp. cultivar that produces a unique essential oil, produces more oil on a dry weight basis and has a compact plant type and resistance to mint rust (*Puccinia menthae*).

2 Drawing Sheets

Latin name of the genus and species: *Mentha* sp.
Variety denomination: 'BOULDER MINT'.

TYPE OF PLANT AND NAME OF VARIETY

The present invention relates to a new and distinct variety of peppermint plant developed from a parent of the species *M. arvensis*. The new variety will be identified as 'Boulder Mint'.

BACKGROUND OF INVENTION

This new mint was developed in a mint breeding program in which the primary objective was to develop a Mitcham type peppermint variety having a specific oil composition, acceptable yield and resistant to mint diseases. The new variety is as susceptible to mint wilt (soil borne fungus *Verticillium dahliae*) as its parent, but more resistant to mint rust (airborne fungus *Puccinia menthae*). No rust has been observed on 'Boulder Mint' since 2007 and subsequent years. 'Boulder Mint' has a higher yield of oil than the control variety, 'Black Mitcham', in test plots since 2007. This plant was selected from a population of mint seedlings in research plots on land near Monmouth, Oreg. and initially identified as 07-A3-5A.

DISCOVERY AND ASEXUAL REPRODUCTION

'Boulder Mint' originated as a seedling from an open pollinated *Mentha arvensis,* 06-Blanco-5-A, a female parent included with other *M. arvensis* and male fertile *M. piperita* plants in a polycross breeding program. Diploid *M. piperita* is sterile and only becomes fertile in the polyploidy state. The parent plants in the polycross breeding system were composed of selected fertile male and female genotypes based on certain desirable characteristics.

'Boulder Mint' is asexually propagated, by tip cuttings and stolon sections, to maintain the cultivars genetic integrity and as a means of increasing the selection for commercial planting. Asexual propagation, by tip cuttings or stolon sections, is a common practice in commercial mint cultivation and serves as a means of propagating the normally sterile mint plant. The inventor has conducted asexual propagation of 'Boulder Mint' for greenhouse and field planting at Monmouth, Oreg., since 2007 and the genotype come true to form with each generation.

SUMMARY OF THE INVENTION

Mint selection 07-A3-5A denominated 'Boulder Mint' is a new *Mentha* sp. cultivar that produces an essential oil different in composition than commercially grown mint varieties.

The essential oil is similar to standard mint oil in components composition but differs in the typical ratio of components. Organoleptically, it differs from typical *Mentha piperita* peppermint oil. It is more resistant to mint rust than current commercially grown *Mentha arvensis* varieties.

BRIEF DESCRIPTION OF THE FIGURES

The accompanying color photographs show the typical, one year old, field grown vegetative growth of 'Boulder Mint' and depicts the color as nearly as reasonably possible.

FIG. 1 illustrates the flowering pattern, multiple flowering shoots, inflorescence spike development, of my new mint plant in accordance with the present invention.

FIG. 2 illustrates the leaf shape and compact growth of my new mint plant.

DESCRIPTION OF PLANT

My new mint plant improves upon and is distinct from other mint plants in several characteristics, including but not limited to, the following:

1. The ability to produce an essential oil different in composition than typical commercial *M. arvensis* or *M. piperita*, but with similar components as 'Black Mitcham' peppermint (*M. piperita*);
2. Produce more oil on a dry weight basis than currently grown mint varieties;
3. A more compact plant but with a branching pattern similar to its parent;
4. An early spring growth similar to 'Black Mitcham' peppermint but with a more vigorous growth through maturity;
5. A level of resistance to mint rust equal to or greater than that of its *M. arvensis*

The essential oil extracted from 'Boulder Mint' has a composition of components that is different than that of commercial oil produced by 'Black Mitcham' peppermint (*M. piperita*) and *M. arvensis* as illustrated in Table 1. The concentration of menthone in oil of 'Boulder Mint' is greater than that of *M. arvensis* and *M. piperita*. There is a trace of menthofuran and pulegone present in the oil of 'Boulder Mint' and absent in oil of its parent and commercial *M. arvensis*. Organoleptically, the oil of 'Boulder Mint' is different than that of 'Black Mitcham' and *M. arvensis*, reflecting the difference in oil component ratios.

TABLE 1

A Comparison of 'Boulder Mint' Oil collected from test plots near Monmouth, Oregon to that of its *M. arvensis* parent, Commercial *M. arvensis*, and Commercial *M. piperita* Oils. 1/

| Essential Oil Components | *Mentha arvensis* Parent seedling 2/ | 'Boulder Mint' Seedling 2/ | Commercial *M. arvensis* | Commercial *M. piperita* |
|---|---|---|---|---|
| 1-Limonene | 3.0 | 1.6 | 3.0 | 1.7 |
| 1,8-Cineole | <1.0 | <1.0 | <1.0 | 4.9 |
| 1-Menthone | 15.7 | 44.2 | 7.3 | 19.4 |
| Menthofuran | 0.0 | <1.0 | 0.0 | 4.2 |
| Isomenthone | 3.5 | 3.1 | 3.6 | 3.1 |
| 1-Menthyl Acetate | 3.7 | 3.5 | 2.9 | 5.3 |

TABLE 1-continued

A Comparison of 'Boulder Mint' Oil collected from test plots near Monmouth, Oregon to that of its *M. arvensis* parent, Commercial *M. arvensis*, and Commercial *M. piperita* Oils. 1/

| Essential Oil Components | *Mentha arvensis* Parent seedling 2/ | 'Boulder Mint' Seedling 2/ | Commercial *M. arvensis* | Commercial *M. piperita* |
|---|---|---|---|---|
| 1-Menthol | 64.3 | 34.1 | 73.9 | 44.6 |
| Pulegone | <1.0 | 1.9 | 0.0 | 2.1 |

The numbers listed in the above table are percentages based upon the analysis of the respective mint oils by gas chromatography. The percentages are determined by calculation of the relative peak areas.
1/ Commercial essential oils of *M. arvensis* and *M. piperita* were what is typically produced by mint growers.
2/ The essential oil of *M. arvensis* parent seedling and 'Boulder Mint' were collected from plants growing in test plots in 2007.

TAXONOMIC DESCRIPTION OF 'BOULDER MINT'

This new plant, under greenhouse and field growing conditions, is a bush type plant with lateral branches at each node of the main stems. The height of 'Boulder Mint' is 75-90 cm and is equal to or greater than 'Black Mitcham' growing under similar conditions and will vary based on fertilizer, soil quality, and water application, amongst other known factors that affect growth patterns. Secondary and tertiary branching occurs to form a compact growth habit. The main stem at mid-plant (approximately between the eleventh and twelfth node) of a mature plant is 4.4-5.2 mm in width. The secondary and tertiary branch stems are 1.9-2.2 mm and 1-2 mm in width, respectively. The average plant width is 25 cm and the average length of the main stem is 76 cm. The stems are square, glabrous, and a green color that matches Fifth Edition Royal Horticultural Society Colour Chart 143B green group.

Mature leaves at the bottom of the plant are ovate lanceolate as are leaves on secondary branch stems. Leaves on upper mature plants, both main and secondary stems are more lanceolate (FIG. 2). Mid-main stem leaf size at flowering is 30-34 mm in width and 63-68 mm in length. Leaf size on secondary branches at flowering is 18-24 mm in width and 38-44 mm in length. Leaf petioles on the main stem leaves are 10-16 mm in length while petioles on secondary branch stem leaves are 4-7 mm in length. Leaves on the mid-main and lower stem tend to be less dentate than 'Black Mitcham' peppermint leaves while the leaves on the upper plant tend to be more dentate and similar to 'Black Mitcham' peppermint leaves. The main stem leaves have from 16 to 18 teeth on each side while the secondary branch leaves have 10-14 teeth on each side. The adaxial leaf surface is glabrous and green in color, ranging from Fifth Edition Royal Horticultural Society Colour Chart N137B to N137C in the green group classification. The abaxial leaf surface is sub-glabrous with oil glands distributed across the surface and is light green in color as illustrated in The Fifth Edition Royal Horticultural Society Colour Chart 138A green group. The leaf has 6-9 lateral veins, more or less in parallel off the main vein that runs from the petiole to the tip of the leaf. The veins are prominent in all leaves of 'Boulder Mint'.

The inflorescence is a conspicuous spike with capitate flowers developing at the nodes of the spike stem. The cylindrical spikes are about 30 mm in diameter, and is indeterminate, and may be up to 250 mm in length. The capitate flowers are 15-20 mm in width and 10-15 mm in length. The flowers consist of five petals fused into a two lipped corolla. The corolla is violet in color as illustrated in The Fifth Edition Royal Horticultural Society Colour Chart 84D in the Violet Group. The calyx is generally yellow green and is 143A to 143B RHS, Green Group as illustrated in The Fifth Edition Royal Horticultural Society Colour Chart index. The gynoecium consists of a single pistil with two lobed stigma that is exserted. The androecium consists of four stamens, each with a distinct filament and anther.

While the plant that comprises the present invention has been described in connection with a specific embodiment thereof, it will be understood that this application is intended to cover any variation, uses, or adaptation of the invention (particular those induced by cultivation under different environmental conditions) following, in general the principles of the invention and including such departures from the present disclosure as come within known or customary practice in the art to which the invention pertains and as may be applied to the essential features hereinbefore set forth, and as fall within the scope of the invention and the limits of the appended claim.

I claim:

1. A new and distinct variety of peppermint plant, substantially as shown and described, characterized particularly by improving resistance to mint rust, and producing a unique essential oil.

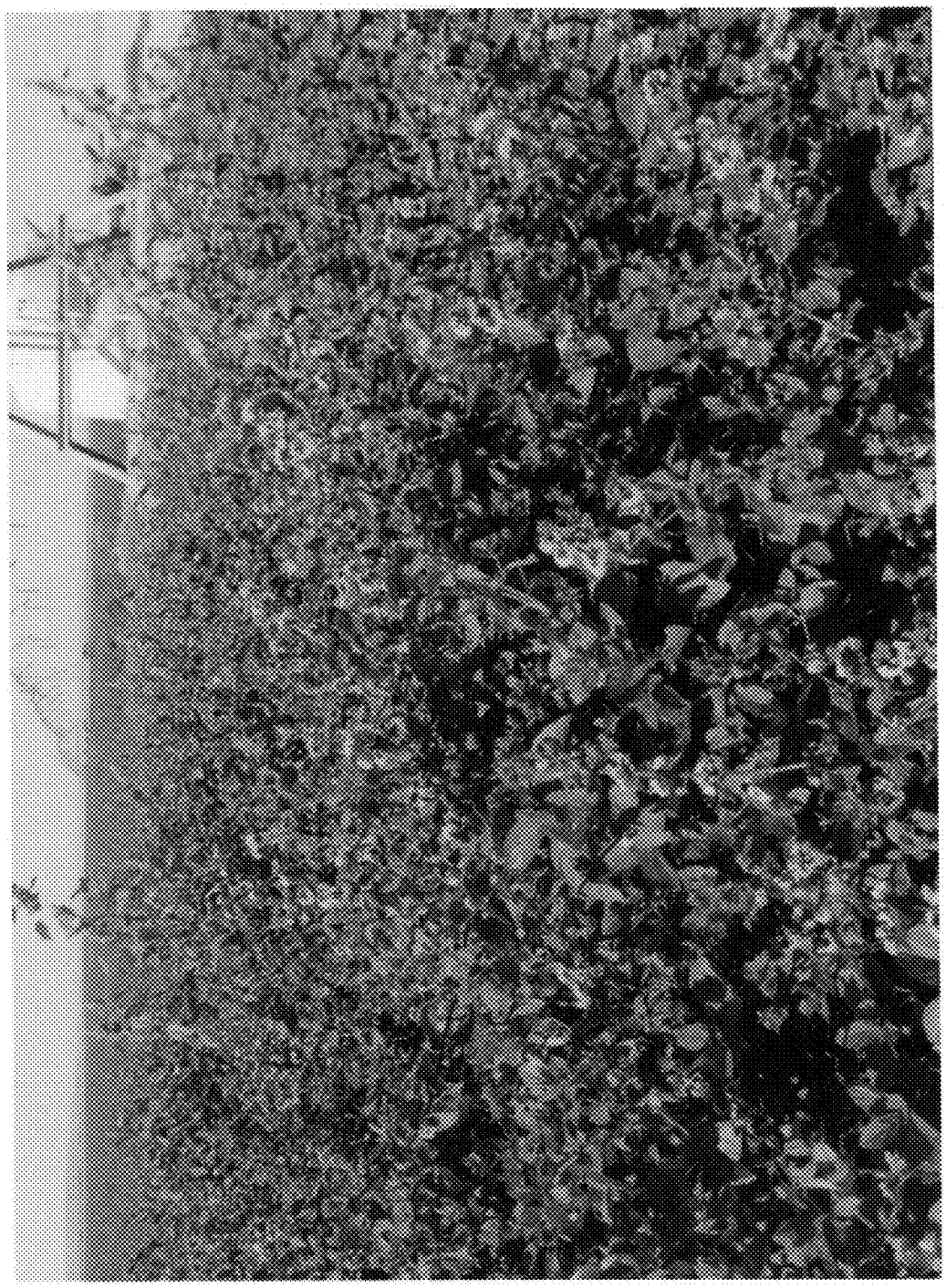

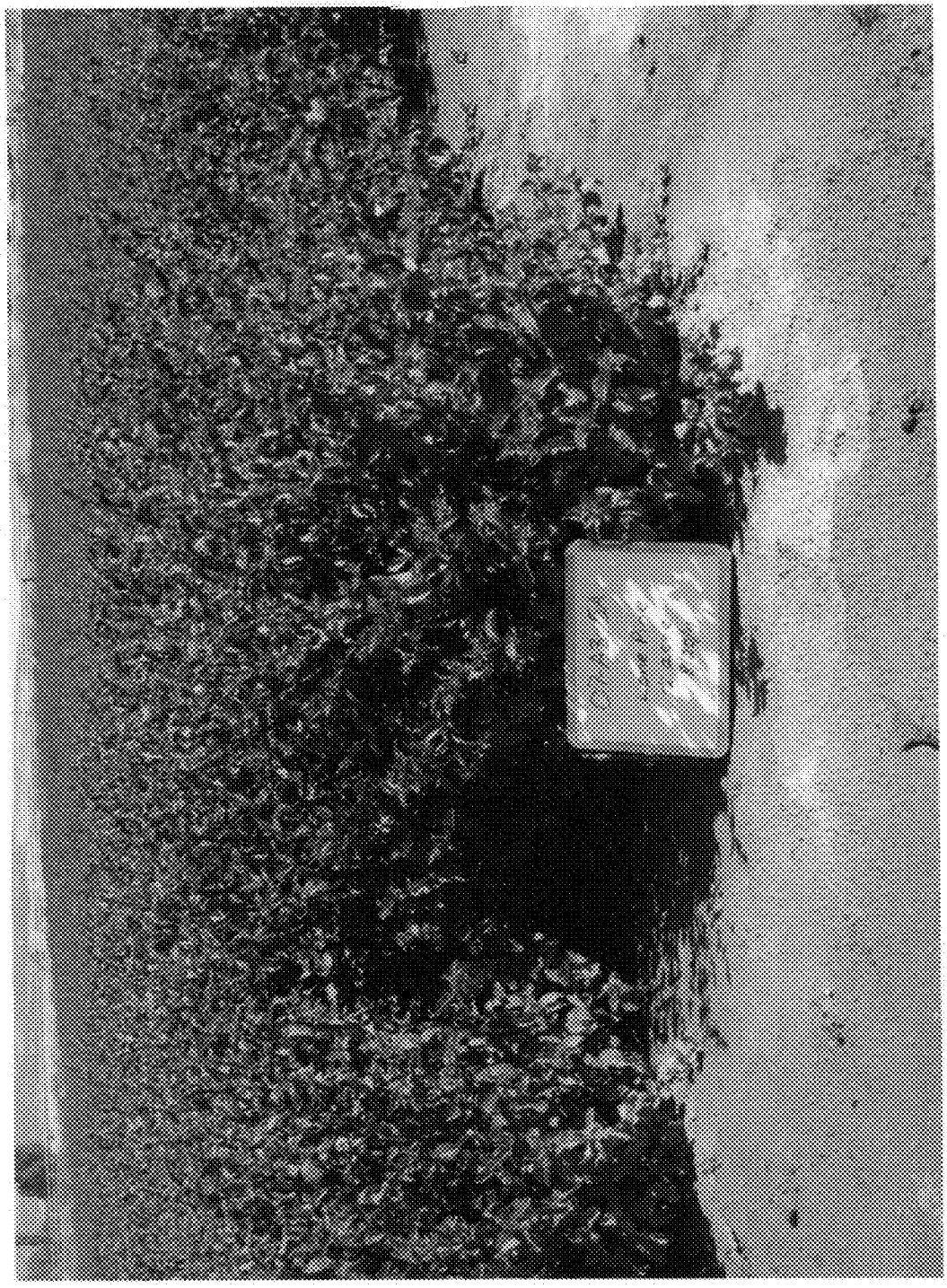

* * * * *